United States Patent
Fischer et al.

(10) Patent No.: US 9,259,070 B2
(45) Date of Patent: Feb. 16, 2016

(54) HAIR CARE PRODUCTS CONTAINING CONJUGATED UNSATURATED OILS

(71) Applicant: Kao Corporation, Tokyo (JP)

(72) Inventors: Vincent Fischer, St. Petersburg, FL (US); Suzanne Dawis, Florence, KY (US); Adam Schrott, Cincinnati, OH (US); Jennifer Deardorff, Liberty Township, OH (US)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/940,600

(22) Filed: Jul. 12, 2013

(65) Prior Publication Data

US 2013/0298932 A1    Nov. 14, 2013

Related U.S. Application Data

(62) Division of application No. 13/051,025, filed on Mar. 18, 2011.

(60) Provisional application No. 61/315,529, filed on Mar. 19, 2010.

(51) Int. Cl.
| | |
|---|---|
| *A61Q 5/12* | (2006.01) |
| *A45D 7/04* | (2006.01) |
| *A45D 7/02* | (2006.01) |
| *A45D 7/06* | (2006.01) |
| *A61K 8/92* | (2006.01) |
| *A45D 7/00* | (2006.01) |
| *A45D 19/00* | (2006.01) |

(52) U.S. Cl.
CPC .. *A45D 7/04* (2013.01); *A45D 7/02* (2013.01); *A45D 7/06* (2013.01); *A61K 8/922* (2013.01); *A61Q 5/12* (2013.01); *A45D 2007/002* (2013.01); *A45D 2019/0041* (2013.01)

(58) Field of Classification Search
None
See application file for complete search history.

(56) References Cited

U.S. PATENT DOCUMENTS

| | | | |
|---|---|---|---|
| 2003/0086897 A1* | 5/2003 | Ohta et al. | 424/70.23 |
| 2007/0154432 A1* | 7/2007 | Davis | 424/70.12 |
| 2007/0166260 A1* | 7/2007 | Monks et al. | 424/70.11 |
| 2010/0016271 A1* | 1/2010 | Chang et al. | 514/188 |

FOREIGN PATENT DOCUMENTS

WO    WO 99/17713    *    4/1999

* cited by examiner

*Primary Examiner* — Jyothsna Venkat
(74) *Attorney, Agent, or Firm* — Frost Brown Todd LLC

(57) ABSTRACT

Hair care products for providing long-lasting conditioning, moisturizing, split end repair, body, volume, shine and increased hair strength benefits are disclosed. The products can be in the form of shampoos, conditioners, serums or oils, and comprise a compatible hair care carrier together with an unsaturated oil having an iodine value of at least about 80, and wherein the oil is selected from glycerol triesters of fatty acids wherein the fatty acids have a composition selected from:
(a) less than 18% oleic acid (C18:1) and greater than 30% linoleic acid (C18:2);
(b) less than 10% oleic acid (C18:1) and greater than 65% linolenic acid (C18:3);
(c) greater than 50% eleostearic acid; and
(d) mixtures thereof.
The method of conditioning hair using the defined products is also disclosed.

3 Claims, No Drawings

HAIR CARE PRODUCTS CONTAINING CONJUGATED UNSATURATED OILS

This application is a divisional of U.S. patent application Ser. No. 13/051,025, filed Mar. 18, 2011, titled Hair Care Products Containing Conjugated Unsaturated Oils. This application is also related to and claims priority from U.S. Provisional Patent Application No. 61/315,529, filed Mar. 19, 2010. These applications are incorporated herein by reference in their entirety.

TECHNICAL FIELD

The present invention relates to wash-out or leave-in hair care products, such as shampoos, conditioners or serums, which are used to provide hair conditioning and other hair care benefits to the user.

BACKGROUND

Hair conditioning products are well-known; they are used to provide a wide range of benefits to the user. Examples of such benefits include conditioning, moisturizing, split end repair, and enhanced body, volume, shine and/or strength. These types of products are frequently used as leave-on products, i.e., they are applied after the hair is washed, and left on the hair until the next washing. However, combination products which provide both cleaning and a hair conditioning benefit are also quite well-known.

A variety of materials have been used in the art to provide these hair care benefits. Examples of such materials include silicones, waxes (see, for example, U.S. Published Patent Application 2007/0184007), quaternary ammonium materials, pre-formed polymers, and monomeric materials which are not polymerized (see, for example, U.S. Published Patent Application 2009/0104136). While each of these components can be formulated to provide desirable hair care and hair conditioning benefits, each also has certain formulational and usage limitations. For example, silicones, waxes and quaternary ammonium materials can leave hair with a greasy/oily look and feel, if not used correctly, and at precisely the correct levels. Further, polymers in hair care products can exhibit efficacy and longevity issues. For example, many existing hair care treatments are not robust (i.e., long-lasting) and can lose their efficacy over the course of a day. Many treatments lose their efficacy upon exposure to water or excess humidity. In addition, many hair treatments weigh down hair, flake off, leave unsightly residues, fail to dry and set quickly, do not provide adequate hold, and are not effective for hard to treat hair, such as naturally curly hair. Treatments have been developed which overcome some of these issues; however, they typically involve permanently treating the hair with reducing and/or oxidizing agents, which can damage hair. Thus, there remains a need for hair treatments that withstand the rigors of a typical user's daily routine and can maintain efficacy in a variety of environments without damaging hair fibers. There is, therefore, a desire to formulate a composition which provides styling and/or conditioning benefits to hair using simple molecules which are easy to obtain and formulate, provide long-lasting benefits, and avoid the build-up of waxy, oily or scaly residue on the hair.

Conjugated unsaturated oils, derived from vegetables, nuts or fish, are generally known. Such materials include, for example, sunflower oil, soybean oil, peanut oil, rapeseed oil, linseed oil, canola oil, walnut oil, corn oil, tung oil, and flaxseed oil. They are frequently used for cooking and, even, furniture finishing. Some vegetable and nut oils have been used in hair care products. Examples of such oils include olive oil and linseed oil, which have been used in hair conditioning products; see, for example, The Body Shop Rainforest Radiance Conditioner (linseed oil); Softee Extra Virgin Olive Oil Hair and Scalp Conditioner; and Kiehl's Since 1851 Sunflower Oil Color Preserving Conditioner. Those oils do not have high iodine values (i.e., they are not sufficiently unsaturated) and are not formulated to polymerize to any significant degree on the hair.

Drying oils, having high iodine values, are known for use in formulating oil paints, varnishes and other coating compositions. They provide this coating effect after application to a surface by polymerizing when exposed to oxygen in the atmosphere. Drying oils have not heretofore been used in hair compositions in a formulation which allows crosslinking and polymerization thereby providing a styling and/or conditioning benefit to the hair; such compositions provide enhanced efficacy and longevity of the conditioning benefit.

U.S. Published Patent Application 2007/0184007, Walter et al, published Aug. 9, 2007, describes a form of wax composition which is said to be non-yellowing and which can advantageously be used in hairstyling products. The materials disclosed are fully esterified di- or oligosaccharide polyesters, and particularly octaesters of sucrose with $C_8$-$C_{30}$ fatty acids, such as benenic acid and fatty acids derived from cotton seed oil.

U.S. Published Patent Application 2009/0104136, Anderson et al, published Apr. 23, 2009, defines a method of obtaining hair conditioning and styling through the application of specific compounds, such as octafluoropentyl methacrylate (OFPMA). The disclosed method, which utilizes these materials, does not rely on heating of the hair or application of a free-radical initiator or a heat-activated initiator to polymerize the materials. In fact, it is taught that the materials do not polymerize on the hair.

SUMMARY

The present invention relates to hair care products which comprise an unsaturated oil having an iodine value of at least about 80 (and preferably at least about 120) and a compatible hair care carrier, wherein the product is formulated such that the oil deposits on the hair to which it is applied and polymerizes, forming a film on the hair upon exposure to oxygen in the atmosphere, and further wherein the oil is selected from gylcerol triesters of fatty acids wherein the fatty acids have a composition selected from:

(a) less than 18% oleic acid (C18:1) and greater than 30% linoleic acid (C18:2);

(b) less than 10% oleic acid (C18:1) and greater than 65% linolenic acid (C18:3);

(c) greater than 50% eleostearic acid; and (d) mixtures thereof.

Examples of such oils include rose hip seed oil, poppy seed oil, safflower oil, wheat germ oil, inca inchi oil, grapeseed oil, tung oil, bitter gourd seed oil, and mixtures thereof.

The present invention also encompasses a method of providing conditioning to hair comprising applying to wet hair an effective amount of a hair care product comprising an unsaturated oil having an iodine value of at least about 80, and preferably at least about 120, and a compatible hair care carrier, wherein the said product is formulated such that said oil polymerizes and forms a film on the hair upon exposure to oxygen in the atmosphere, and further wherein the oil is selected from glycerol triesters of fatty acids wherein the fatty acids have a composition selected from:
  (a) less than 18% oleic acid (C18:1) and greater than 30% linoleic acid (C18:2);
  (b) less than 10% oleic acid (C18:1) and greater than 65% linolenic acid (C18:3);
  (c) greater than 50% eleostearic acid; and
  (d) mixtures thereof.

In one embodiment of the method, heat is applied to the wet hair (such as by using a hair dryer, flat iron or curling iron) after the product has been applied to the hair.

As used herein, all percentages and ratios are "by weight", unless otherwise specified. Further, all references listed in this application are incorporated herein by reference.

DETAILED DESCRIPTION

The present invention relates to hair care products which comprise an unsaturated oil having an iodine value of at least about 80, and having specifically-defined fatty acid compositions, together with a compatible hair care carrier. The product is formulated such that the oil component deposits on the hair and polymerizes upon exposure to oxygen in the atmosphere thereby forming a film on the hair to which it has been applied. It is this film which provides a long-lasting hair conditioning benefit to the user. The method of conditioning hair using the defined compositions is also disclosed herein.

The hair care products which can be formulated as embodiments of the present invention include both wash-off and leave-on hair products. For example, the products may include shampoos, conditioners, sprays, serums or oils, and can provide the user with benefits ranging from hair cleaning, hair conditioning, hair moisturizing, split-end repair, as well as enhanced body, volume, shine, and hair strength. Leave-on products, such as conditioners and serums, are preferred since they generally represent a more efficient way to deliver the hair care active than do wash-off products since, in wash-off products, the active is applied and then, at least a portion, is washed off leaving just the residue to provide the hair care benefit. The hair care products encompassed within the present invention are well-known in the hair care arts, including their conventional components and methods of formulation.

A required component of the hair care products of the present invention is the unsaturated oil. The hair care products contain from about 0.01% to about 90%, preferably from about 0.01% to about 25%, more preferably from about 0.1% to about 10% of the oil component. The oil must have an iodine value at least about 80, and preferably at least about 120.

The iodine value of a compound is the mass of iodine in grams that is consumed by 100 grams of a chemical substance. An iodine solution is yellow/brown in color and any chemical group in the substance that reacts with iodine will make the color disappear at a precise concentration. The amount of iodine solution thus required to keep the solution yellow/brown is a measure of the amount of iodine sensitive reactive groups in a chemical compound. One application of the iodine number is a determination of the amount of unsaturation contained in fatty acids. This unsaturation is in the form of double bonds which react with iodine compounds. The higher the iodine number, the more unsaturated fatty acid bonds are present in a fatty material. In a typical procedure, the acid is treated with an excess of the Hanus or Wijs solutions, which are, respectively, solutions of iodine monobromide (IBr) and iodine monochloride (ICl) glacial acetic acid. Unreacted iodine monobromide (or monochloride) is reacted with potassium iodine, converting it to iodine, whose concentration can be determined by titration with sodium thiosulfate. Standard methods for iodine value analysis are, for example, disclosed in ASTM D5768-02 (2006) and DIN 53241 (both incorporated herein by reference). See also Pocklington, Determination of the Iodine Value of Oils and Fats, Pure & Appl. Chem. 62(12):2339-2343 (1990), incorporated herein by reference.

The unsaturated oils utilized in the present invention, after application to the hair, oxidize upon exposure to oxygen in the atmosphere and in so doing polymerize to form a film on and/or in hair strands. These films provide the desired hair conditioning properties. The reactivity (and film-forming ability) of these oils results from the presence of diallylic groups (two double bonds separated by methylene groups, —CH=CHCH$_2$CH=CH—) or conjugated double bonds (two carbon-carbon double bonds separated by a single bond) that, on exposure to air, are oxidized to form cyclic peroxide or hydroperoxide intermediates. These peroxides, in turn, react with another unsaturated side chain and form a radical capable of continued or sustained polymerization. In contrast, the mono-unsaturated (for example, oleic acid, C18:1) fatty acid residues form unstable allylic radical intermediates which offer slow or no polymerization potential for hair care applications.

The unsaturated oils having an iodine value of at least about 120 are also known as drying oils. A drying oil is an oil that hardens to a tough, solid film after a period of exposure to air. The oil does not harden through the evaporation of water or other solvents, but through a chemical reaction in which the components crosslink by the action of oxygen. Drying oils are a key component of oil paint and some varnishes. Some commonly used drying oils include linseed (flax seed) oil, tung oil, poppy seed oil, perilla oil, and walnut oil. The "drying" hardening or, more properly, curing of oils is the result of autoxidation, the addition of oxygen to an organic compound and the subsequent crosslinking of that compound. In this process, $O_2$ inserts into C—H bonds adjacent to double bonds within the unsaturated fatty acids. The resulting hydroperoxides are susceptible to crosslinking reactions. The formation bonds form between neighboring fatty acid chains resulting in a polymer network, often visible by formation of a skin-like film on samples. The resulting material provides stable films which, while somewhat elastic, do not flow or deform readily. Diene-containing fatty acid derivatives, such as those derived from linoleic acid are especially prone to this reaction because they generate pentadienyl radicals. Mono-unsaturated fatty acids, such as oleic acid, are slower to undergo drying because the allylic radical intermediates are less stable (i.e., slower to form).

Drying oils consist of glycerol triesters of fatty acids. These esters are characterized by high levels of polyunsaturated fatty acids, especially alpha-linolenic acid. One common measure of the "siccative" (drying) property of oils is iodine number, which is an indicator of the number of double bonds in the fatty acid components of the oil. Oils having an iodine number greater than about 120, and particularly greater than about 130, are considered drying, those with an iodine number between 115 and 120 are semi-drying, and those with an iodine number less than about 115 are non-drying.

Examples of oils which can be used in the compositions of the present invention include rose hip seed oil, poppy seed oil, safflower oil, wheat germ oil, inca inchi oil, grapeseed oil, tung oil, bitter gourd seed oil, and mixtures of those materials.

In addition to being defined by the iodine values set forth above, the oils which may be utilized in the present invention are glycerol triesters of fatty acids wherein the fatty acid has a composition selected from:

(a) less than 18% oleic acid (C18:1) and greater than 30% linoleic acid (C18:2);

(b) less than 10% oleic acid (C18:1) and greater than 65% linolenic acid (C18:3);

(c) greater than 50% eleostearic acid; and (d) mixtures thereof.

The following table lists several common oil materials and indicates how they fall within this definition of useful oils for the present invention.

|  | C14 Myristic | C16 Palmitic | C18 Stearic | C18:1 Oleic | C18:2 Linoleic | C18:3 Linolenic | C20 Arachidic | C22 Behenic | C22:1 Erucic | C24 Lignoceric | C18:3 α-Eleostearic |
|---|---|---|---|---|---|---|---|---|---|---|---|
| Olive | 0 | 8 | 2 | 84 | 6 | 0 | 0 | 0 | 0 | 0 | 0 |
| Sunflower | 0 | 6 | 6 | 20 | 68 | 0 | 0 | 0 | 0 | 0 | 0 |
| Soybean (Soja) | 0 | 7 | 4 | 29 | 54 | 6 | 0 | 0 | 0 | 0 | 0 |
| Peanut | 0 | 7 | 5 | 59 | 23 | 0 | 3 | 1 | 0 | 2 | 0 |
| Rapeseed | 0 | 2 | 1 | 21 | 20 | 2 | 1 | 0 | 53 | 2 | 0 |
| Linseed | 0 | 5 | 2 | 17 | 15 | 61 | 0 | 0 | 0 | 0 | 0 |
| Safflower | 0 | 6 | 2.5 | 12 | 75 | 0.5 | 0 | 0 | 0 | 0 | 0 |
| Canola | 0 | 3 | 77 | 14 | 6 | 0 | 0 | 0 | 0 | 0 | 0 |
| Cottonseed | 1 | 22 | 2 | 32 | 44 | 0 | 0 | 0 | 0 | 0 | 0 |
| Walnut | 0 | 6 | 4 | 26 | 48 | 16 | 0 | 0 | 0 | 0 | 0 |
| Wheat | 0 | 16.5 | 5.5 | 11.5 | 57 | 9 | 0 | 0 | 0 | 0 | 0 |
| Corn | 0 | 8 | 4 | 46 | 42 | 0 | 0 | 0 | 0 | 0 | 0 |
| Poppy | 0 | 10 | 2 | 15 | 73 | 0 | 0 | 0 | 0 | 0 | 0 |
| Grape Seed Oil | 0 | 10 | 0 | 3 | 17 | 70 | 0 | 0 | 0 | 0 | 0 |
| Tung | 4 | 1 | 0 | 7 | 7 | 1 | 0 | 0 | 0 | 0 | 80 |
| Flaxseed | 0 | 6.5 | 2.5 | 19 | 24 | 47.5 | 0 | 0 | 0 | 0 | 0 |
| Rose Hip Seed Oil | 0 | 4 | 2 | 15.5 | 45.5 | 33.5 | 0 | 0 | 0 | 0 | 0 |
| Inca Inchi | 0 | 4 | 3 | 10 | 35 | 47 | 0 | 0 | 0 | 0 | 0 |

The second component of the compositions of the present invention is a compatible carrier known for use in hair care compositions. Such materials are well-known in the hair care product formulation arts. The carrier needs to be safe for application to the head and hair and be compatible with other ingredients contained in the hair care product. Examples of such materials include water, ethanol, silicones, mineral oil, esters (e.g., isopropyl myristate and isopropyl palmitate), and other solvents commonly used in the hair care art, and mixtures thereof.

Additional components known for use in hair care compositions may also be included for their known uses at their art-established levels. Examples of such materials include conditioners, surfactants, preservatives, dyes, perfumes, vitamins, anti-oxidants, lubricants, pH control agents, moisturizers, rheology control agents, combing acids, static control aids, and formulational aids.

The hair care compositions of the present invention are made in a conventional manner. For example, rinse off conditioner compositions are made using conventional techniques known in the art. A possible procedure follows. In the main vessel, add purified water and heat to 80 C. Add components (A) which include water-soluble ingredients (such as pH regulators, salts, glycerin). Mix until homogenous. Components (B) comprise the "oil phase" and should be pre-mixed in a separate vessel, heated to 80 C, and mixed until homogeneous. The oil phase components are added to the main vessel with mixing to form an emulsion. The resulting emulsion is cooled to 40 C, and the remaining components (C) may beaded with sufficient mixing to incorporate them into the emulsion.

Serum, Oil Treatments, and Conditioning Oil compositions are made using conventional techniques known in the art. A possible procedure is as follows; In a suitable vessel, add ingredients individually to main tank with sufficient mixing to ensure homogeneity.

Shampoo compositions are made using conventional techniques known in the art. A possible procedure follows. In the main vessel, add purified water and heat to 80 C. Add components (A) which include water-soluble ingredients (such as pH regulators, salts, surfactants). Mix until homogeneous. Components (B) comprise the "oil phase" and should be pre-mixed in a separate vessel, heated to 80 C, and mixed until homogeneous. The oil phase components are added to the main vessel with mixing to form an emulsion. The resulting emulsion is cooled to 40 C, and the remaining components (C) may be added with sufficient mixing to incorporate them into the emulsion.

The present invention also encompasses a method for providing hair conditioning and hair care benefits using the products of the present invention. Such hair care benefits include, but are not limited to cleaning, conditioning, moisturizing, split end repair, as well as enhanced body, volume, shine, and strength. It is the formation of the film on the hair (either on the surface of the hair strands and/or bonding into the hair strands) which provides the hair care benefits or which bonds other hair conditioning components contained in the compositions onto the hair thereby providing the hair care benefits. In either event, the presence of the film provides a long-lasting benefit which eventually will wash off as the hair is shampooed. In the method of the present invention, the compositions defined above are applied to the hair, either as part of a washing process, or after the washing is completed as a rinsing process when used as a leave-on product. The unsaturated oil which remains on the hair then polymerizes upon exposure to oxygen in the atmosphere. The hair care benefit can be provided immediately and/or built-up over time (based on repeated deposition of the unsaturated oil materials and ongoing polymerization).

Although it is not necessary, after application of the compositions of the present invention to the hair, heat can be applied to the hair. The application of heat, such as using a hairdryer, flat iron or curling iron, can speed up the benefit obtained by speeding up the polymerization reaction. In addition, it may be possible to use an oxidizer, other than oxygen in the air, to form the film from the compositions of the present invention. Such oxidizing materials could include hydrogen peroxide and bromates. Any oxidizer used in the preparation of personal care products, which is compatible with the rest of the composition, can be used. The use of these oxidizers could lead to a quicker polymerization reaction. The oxidizers would be used at low levels which would encourage polymerization of the applied oils (such as from about 0.01% to about 10% of the composition).

The unsaturated oils defined herein can be incorporated in any hair care product that has the ability to deposit the oil in or on the hair (this could include shampoos that form coacervates).

Examples

Conditioners, serum/oil compositions and shampoos of the present invention are formulated using the components listed in the following tables, using the procedures defined above.

| | Conditioner Compositions | 1 | 2 | 3 | 4 | 5 | 6 | 7 | 9 |
|---|---|---|---|---|---|---|---|---|---|
| A | Water | Balance | Balance | Balance | Balance | Balance | Balance | Balance | Balance |
| | pH Regulator (Lactic Acid, Malic Acid, Tartaric Acid, Fumaric Acid Isonanoic Acid) | qs. | qs. | qs. | qs. | qs. | qs. | qs. | qs. |
| | Glycerin | | | 1.00 | | | | 1.00 | 1.00 |
| B | Cetearyl Alcohol | 5.00 | 5.00 | 5.00 | 5.00 | 5.00 | 5.00 | 6.00 | 6.00 |
| | Cetyl Esters | | | | | | | 0.50 | 0.50 |
| | Behenamidopropyl Dimethylamine | 1.50 | 1.50 | | | 1.50 | | 1.50 | |
| | Cetrimonium Chloride (30% Active) | | | 5.00 | 5.00 | | 5.00 | | 5.00 |
| | Wheat Germ Oil | 5.00 | | | | 0.15 | | | |
| | Inca Inchi Oil | | 0.20 | | | | | 0.15 | 1.00 |
| | Tung Oil | | | 0.20 | | | | | |
| | Safflower Oil | | | | 2.50 | | | 0.20 | |
| | Poppy Seed Oil | | | | | 0.55 | | | 0.25 |
| | Grapeseed Oil | | | | | | 0.35 | | 2.00 |
| C | Preservative (Choice) | qs. | qs. | qs. | qs. | qs. | qs. | qs. | qs. |
| | Fragrance | qs. | qs. | qs. | qs. | qs. | qs. | qs. | qs. |

| | Serum/Oil Composition | 1 | 2 | 3 | 4 | 5 | 6 | 7 | 8 | 9 | 10 | 11 | 12 | 13 |
|---|---|---|---|---|---|---|---|---|---|---|---|---|---|---|
| A | Cyclopentasloxane | Balance | Balance | Balance | | | | | Balance | Balance | Balance | Balance | Balance | Balance |
| | Caprylyl Methicone | | | | | | | | 3.00 | | | | 5.00 | |
| | Isopropyl Palmitate | | | | Balance | Balance | | | | | | | | |
| | Mineral Oil | | | | | | Balance | Balance | | | | | | |
| | Trisiloxane | 2.00 | | 5.00 | 4.00 | | | | | | | | 4.00 | 10.00 |
| | Dimethicone (5 cSt) | 2.00 | | | | 3.00 | | | | | | | | |
| | Dimethicone (10 cSt) | 2.00 | 2.00 | | 3.00 | | | | | | 3.00 | | | |
| | Dimethicone (350 cSt) | 6.00 | | | | | 3.00 | | | | | | | |
| | Dimethicone (20 cSt + Gum) | | 2.00 | | 4.00 | | | | | | 4.00 | | | |
| | Wheat Germ Oil | 2.00 | | | | | | | | | | | | |
| | Inca Inchi Oil | | 0.25 | | 0.25 | | | 0.25 | | | 0.10 | | 0.25 | |
| | Tung Oil | | | 0.05 | | | | | | | | | 0.05 | |
| | Safflower Oil | | | | | | 1.50 | | 1.50 | | 8.00 | | | 0.50 |
| | Poppy Seed Oil | | | | | 0.15 | | | | 0.35 | | | | 0.30 |
| | Grapeseed Oil | | | | | | | 0.60 | | | | 0.65 | 0.25 | |
| | Fragrance | qs | qs | qs | qs | qs | qs | qs | qs | qs | | qs | qs | qs |

| | Shampoo Formulation | 1 | 2 | 3 | 4 | 5 | 6 | 7 |
|---|---|---|---|---|---|---|---|---|
| A | Water | Balance | Balance | Balance | Balance | Balance | Balance | Balance |
| | Sodium Laureth Sulfate (70%) | 14.00 | 14.00 | 14.00 | 14.00 | 14.00 | 14.00 | 14.00 |
| | Sodium Lauryl Sulfate (30%) | 13.50 | 13.50 | 13.50 | 13.50 | 13.50 | 13.50 | 13.50 |
| | Cocamidopropyl Betaine (30%) | 6.50 | 6.50 | 6.50 | 6.50 | 6.50 | 6.50 | 6.50 |
| | Disodium EDTA | 0.05 | 0.05 | 0.05 | 0.05 | 0.05 | 0.05 | 0.05 |
| | Polyquaternium-10 | 0.60 | | | | | | 0.60 |
| | Cationic Guar Gum | | 0.40 | 0.40 | 0.40 | 0.40 | 0.40 | |
| B | Cocamide MEA | 0.60 | 0.75 | 0.75 | 0.75 | 0.75 | 0.75 | 0.75 |
| | EGDS | 1.75 | 1.75 | 1.75 | 1.75 | 1.75 | 1.75 | 1.75 |
| | Cetyl Alcohol | 0.75 | 0.75 | 0.75 | 0.75 | 0.75 | 0.75 | 0.75 |
| | Benzyl Alcohol | 0.50 | 0.50 | 0.50 | 0.50 | 0.50 | 0.50 | 0.50 |
| | Wheat Germ Oil | 0.10 | | | | | | 1.00 |
| | Inca Inchi Oil | 0.10 | 0.25 | | | | | |
| | Tung Oil | 0.10 | | | | 0.05 | | |
| | Safflower Oil | | | 0.30 | | | | 2.00 |
| | Poppy Seed Oil | | | | 0.20 | | | |
| | Grapeseed Oil | | | | | | 0.50 | 0.50 |

-continued

| Shampoo Formulation | 1 | 2 | 3 | 4 | 5 | 6 | 7 |
|---|---|---|---|---|---|---|---|
| C Fragrance | qs. | qs. | qs. | qs. | qs. | qs. | qs. |
| Preservative (Choice) | qs. | qs. | qs. | qs. | qs. | qs. | qs. |
| Viscosity Adjuster (Sodium Chloride) | qs. | qs. | qs. | qs. | qs. | qs. | qs. |
| pH Regulator (Lactic Acid, Malic Acid, Tartaric Acid, Fumaric Acid.) | | | | to pH 5.0-6.0 | | | |

These compositions, when applied to hair, leave a light coating of unsaturated oil on the hair. This coating polymerizes as a result of exposure to oxygen in the atmosphere, leaving the user with a variety of hair conditioning benefits, including moisturizing, split end repair, enhanced body, enhanced volume, enhanced shine, and increased strength.

What is claimed is:

1. A method of providing conditioning to hair comprising applying to wet hair a conditioning effective amount of a hair care product consisting of from about 0.01% to about 25% of an unsaturated oil selected from rose hip seed oil, inca inchi oil, tung oil, bitter gourd seed oil, and mixtures thereof, a compatible hair care carrier selected from the group consisting of water, ethanol, silicones, mineral oils, isopropyl myristate, isopropyl palmitate, and mixtures thereof, and hair care components selected from the group consisting of conditioners, surfactants, preservatives, dyes, perfumes, vitamins, anti-oxidants, lubricants, pH control agents, moisturizers, rheology control agents, combing agents, static control aids, formulational aids, and combinations thereof, wherein said product is formulated such that said oil deposits on the hair to which it is applied and polymerizes to form a film on the hair upon exposure to oxygen in the atmosphere, and wherein heat is applied to the wet hair after application of the hair care product.

2. The method according to claim 1 wherein the heat is applied using an appliance selected from hairdryers, flat irons, curling irons and combinations thereof.

3. The method according to claim 1 wherein the product is a leave-on product selected from conditioners and serums.

* * * * *